US00PP34752P2

(12) United States Plant Patent
Lee

(10) Patent No.: US PP34,752 P2
(45) Date of Patent: Nov. 22, 2022

(54) ***THUJA* PLANT NAMED 'BLTP'**

(50) Latin Name: *Thuja plicata*
Varietal Denomination: BLTP

(71) Applicant: Robert Edward Lee, Independence, LA (US)

(72) Inventor: Robert Edward Lee, Independence, LA (US)

(73) Assignee: Plant Development Services Inc., Loxley, AL (US)

( * ) Notice: Subject to any disclaimer, the term of this patent is extended or adjusted under 35 U.S.C. 154(b) by 0 days.

(21) Appl. No.: 17/741,806

(22) Filed: May 11, 2022

(51) Int. Cl.
*A01H 5/12* (2018.01)
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 5/12
See application file for complete search history.

*Primary Examiner* — Kent L Bell
(74) *Attorney, Agent, or Firm* — Cassandra Bright

(57) ABSTRACT

A new and distinct variety of *Thuja* plant named 'BLTP' is disclosed, characterized by a controlled growth habit and fresh green foliage color year-round. Plants of 'BLTP' have been observed to grow to 10 to 13 feet tall at ten years of age, shorter than most commercial varieties. Pruning is not needed to maintain and attractive landscape plant. Tolerance for *Thuja* Blight and humidity have been observed in the new variety. The new cultivar is a *Thuja*, suitable for horticultural purposes.

2 Drawing Sheets

Latin name of the genus and species: *Thuja plicata.*
Variety denomination: 'BLTP'.

BACKGROUND OF THE INVENTION

The new cultivar, hereinafter referred to as 'BLTP', was discovered as part of a breeding program at a commercial nursery in Independence, La. The intention of the breeding program was to develop new *Thuja* varieties with novel plant habits and disease tolerance for commercial purposes. This new discovery is the result of an open-pollination of various *Thuja plicata* varieties conducted by the inventor during 2005 and 2006.

The new variety was first identified as an interesting new plant during 2008 at the same commercial nursery in Independence, La. After identifying the new variety as a potentially interesting selection, the inventor first organized propagation of 'BLTP' by softwood cuttings at the same commercial nursery during the Fall of 2008. The inventor continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'BLTP' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BLTP' These characteristics in combination distinguish 'BLTP' as a new and distinct *Thuja* cultivar:

1. Slower, more controlled growth than the well-known variety 'Green Giant'.
2. Height of 10 to 13 feet at ten years of age.
3. Foliage maintains a fresh green color year-round.
3. Observed tolerance to *Thuja* Blight (*Didymascella thujina*).
5. Well-adapted for humid conditions.
6. No pruning required to maintain an attractive plant shape.

COMPARISON TO PARENT VARIETY

The exact parent varieties cannot be identified.

COMMERCIAL COMPARISON

*Thuja* 'BLTP' can be compared to the commercial variety *Thuja* 'Green Giant', unpatented. Plants are similar in most horticultural characteristics, however, plants of the new variety differ in the following:

1. Mature height of 'BLTP' is about 20 feet; 'Green Giant' can reach an ultimate height around 50 feet.

BRIEF DESCRIPTION OF THE PHOTOGRAPHS

Figure 1:
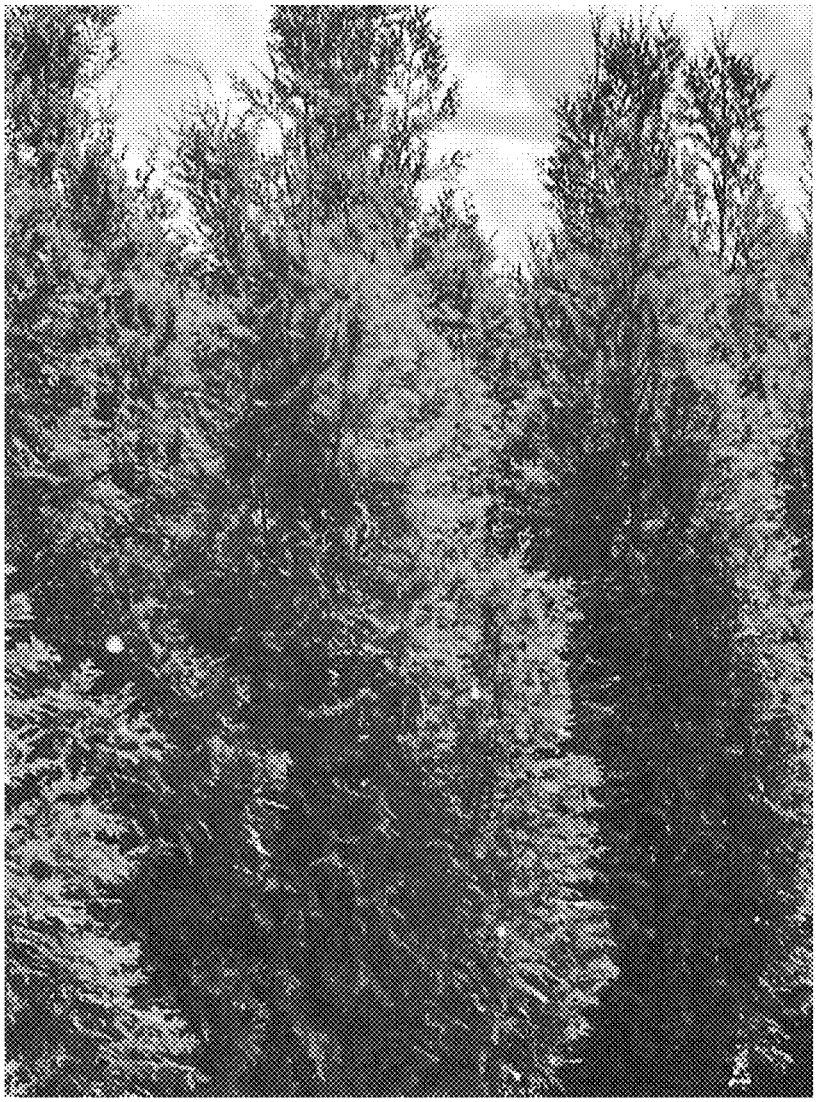

The accompanying photograph in FIG. 1 illustrates in full color typical plants of 'BLTP' grown outdoors in Independence, La. The plants are approximately 8 years old, in the ground.

Figure 2:
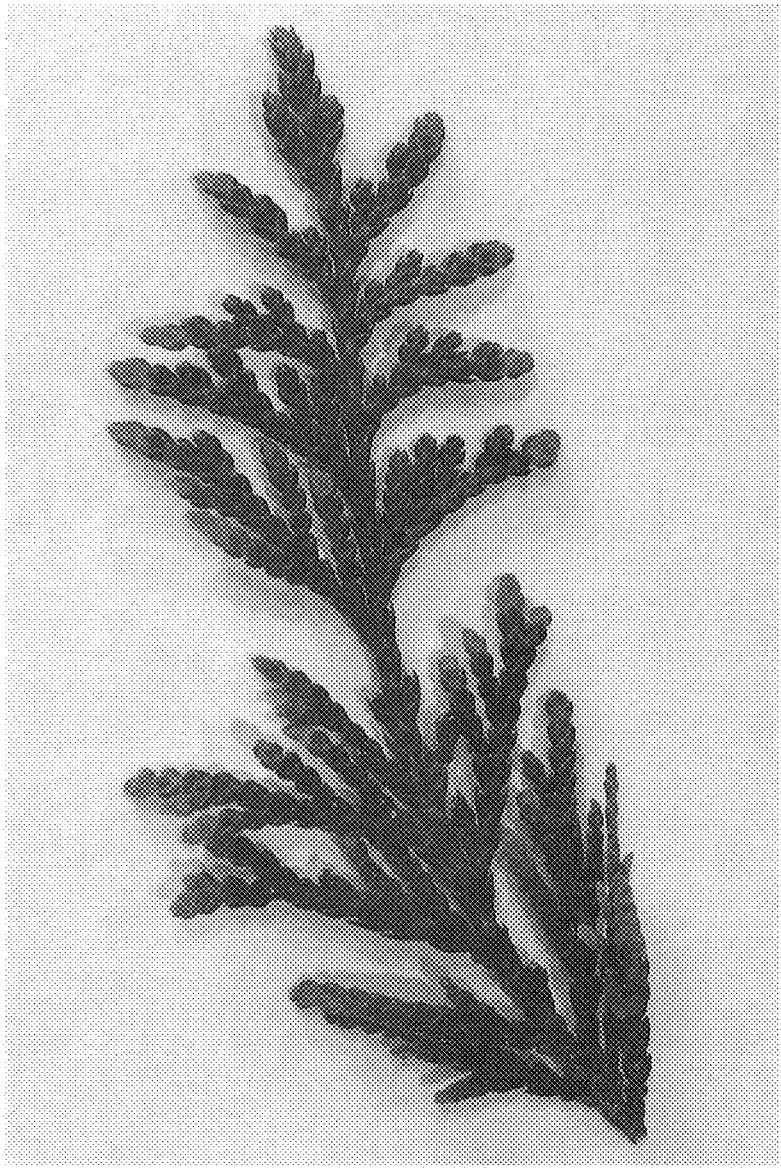

FIG. 2 illustrates a close-up view of a branchlet of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLTP' plants grown outdoors in Loxley, Ala. Plants are approximately 2 to 3 years old, in a 3 gallon nursery container. Measurements and numerical values represent averages of typical plant types.

Botanical classification: *Thuja plicata* 'BLTP'.

PROPAGATION

Time to rooting: About 45 days at approximately 18-27° C.

Root description: Moderately dense branching. Slightly woody, both fine and thick roots present. Colored white and tan, not accurately measured with The R.H.S. chart.

PLANT

Growth habit: Small evergreen tree with a narrow ovate habit.

Height: 40 cm.

Plant spread: 15 cm.

Typical growth rate: Moderate.

Pinching required: No.

Branching characteristics: Upwards at acute angles. Main branches occur at angles of about 15°. Branchlets occur at angles of about 45°.

Average number of main branches: Average 4 major vertical branches.

Length of main branches: Average range 25 to 35 cm.

Diameter of main branches: 7 mm.

Main branch shape in cross section: Oval.

Main branch texture: Rough, scaly.

Lateral branch color:

*Mature*.—Near Grey-Brown 199A tinted Greyed-Red 183C.

*Immature*.—Near Green 137B.

Lateral branch strength: Very strong, flexible.

Branchlet length: 7 to 10 cm.

Branchlet width: 4.5 cm.

Internode length: Average range 1 cm to 1.5 cm between branchlets.

FOLIAGE

Leaf:

*Arrangement*.—Fan-shaped branchlets composed of flattened, alternate, overlapping scales.

*Shape*.—Scales.

*Average length*.—1 mm.

*Average width*.—1 mm.

*Apex*.—Acuminate.

*Base*.—Truncate.

*Margin*.—Entire.

*Texture of top surface*.—Smooth, waxy.

*Texture of bottom surface*.—Smooth, waxy.

*Resin gland*.—Less than 1 mm in diameter, color not distinguishable from leaf blade, appears as a minute, shiny circular structure.

*Color*.—Young foliage upper side: Yellow-Green 144B. Young foliage under side: Yellow-Green 144B. Mature foliage upper side: Green 137A, overlayed 139A. Mature foliage under side: Green 137A, overlayed 139A. Winter foliage: No significant color change.

*Venation*.—Indistinguishable from leaf blade.

*Fragrance*.—Strong, aromatic, somewhat Cedarlike scent.

FLOWER

Flowering not observed.

OTHER CHARACTERISTICS

Disease and pest resistance: Observed tolerance for *Thuja* Blight (*Didymascella thujina*). Neither resistance nor susceptibility of other normal diseases and pets of *Thuja* observed.

Drought tolerance: No tolerance for drought observed.

Temperature tolerance: USDA Zones 5 through 9.

What is claimed is:

1. A new and distinct cultivar of *Thuja* plant named 'BLTP' as herein illustrated and described.

* * * * *